United States Patent
Elliesen et al.

(10) Patent No.: US 6,551,611 B2
(45) Date of Patent: *Apr. 22, 2003

(54) HORMONE REPLACEMENT THERAPY METHOD

(75) Inventors: Jörg Elliesen; Jutta Riedl, both of Berlin (DE)

(73) Assignee: Schering Aktiengesellschaft, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/562,316

(22) Filed: May 1, 2000

(65) Prior Publication Data

US 2002/0142028 A1 Oct. 3, 2002

Related U.S. Application Data

(63) Continuation of application No. 09/288,225, filed on Apr. 8, 1999, now Pat. No. 6,083,528, which is a division of application No. 08/721,968, filed on Sep. 27, 1996, now Pat. No. 5,922,349, which is a continuation-in-part of application No. 08/535,402, filed on Sep. 28, 1995, now abandoned.

(60) Provisional application No. 60/077,182, filed on Sep. 27, 1996.

(51) Int. Cl.[7] ................................................ A61F 13/00
(52) U.S. Cl. ....................... 424/449; 424/434; 424/439; 221/206; 221/207; 222/14; 222/15; 222/71; 222/94; 222/97; 222/544
(58) Field of Search ................................. 424/449, 434, 424/439; 221/206, 207; 222/14, 15, 71, 94, 97, 544

(56) References Cited

U.S. PATENT DOCUMENTS

| | | | |
|---|---|---|---|
| 4,240,146 A | 12/1980 | Iles | 364/467 |
| 4,334,787 A | 6/1982 | Kluth et al. | 366/162 |
| 4,460,109 A | 7/1984 | Ducros et al. | 222/94 |
| 4,687,663 A | 8/1987 | Schaeffer | 424/52 |
| 4,705,783 A | 11/1987 | Crowe et al. | 514/180 |
| 4,826,048 A | 5/1989 | Skorka et al. | 222/137 |
| 4,838,457 A | 6/1989 | Swahl et al. | 222/48 |
| 5,020,694 A | 6/1991 | Pettengill | 222/137 |
| 5,152,432 A | 10/1992 | De Laforcade | 222/145 |
| 5,240,146 A | 8/1993 | Smedley et al. | 222/137 |
| 5,339,990 A | 8/1994 | Wilder | 222/135 |
| 5,478,862 A | 12/1995 | Peters et al. | 514/520 |
| 5,518,734 A | 5/1996 | Stefano et al. | 424/448 |
| 5,922,349 A * | 7/1999 | Elliesen et al. | 424/449 |
| 6,083,528 A * | 7/2000 | Elliesen et al. | 424/449 |

FOREIGN PATENT DOCUMENTS

| | | |
|---|---|---|
| EP | 0 092 473 | 10/1983 |
| WO | 92/15345 | 9/1992 |

OTHER PUBLICATIONS

Vidal 1995, Apr. 6, 1995, Editions du Vidal, pp. 1065–1066; 1219–1220.

* cited by examiner

Primary Examiner—S. Mark Clardy
Assistant Examiner—Michael A. Williamson
(74) Attorney, Agent, or Firm—Millen, White, Zelano & Branigan, P.C.

(57) ABSTRACT

Varying the daily dose of either or both of the estrogen and the progestogen administered for hormone replacement therapy (HRT) is readily and inexpensively accomplished, without the necessity of the physician prescribing a new product each time the daily dose of the estrogen or progestogen is changed, by administering preferably transdermally the estrogen and the progestogen contained in separate extrudable pharmaceutical compositions from a dispenser which contains means, preferably adjustable only by the attending physician or dispensing pharmacist, for varying the volume of either or both of the respective compositions which is dispensed as a single dose from the dispenser in response to a defined digital dispensing manipulation of the dispenser thereby facilitating optimal compliance to a combination of HRT with individually adjusted dosages of the estrogen and progestogen.

16 Claims, 7 Drawing Sheets

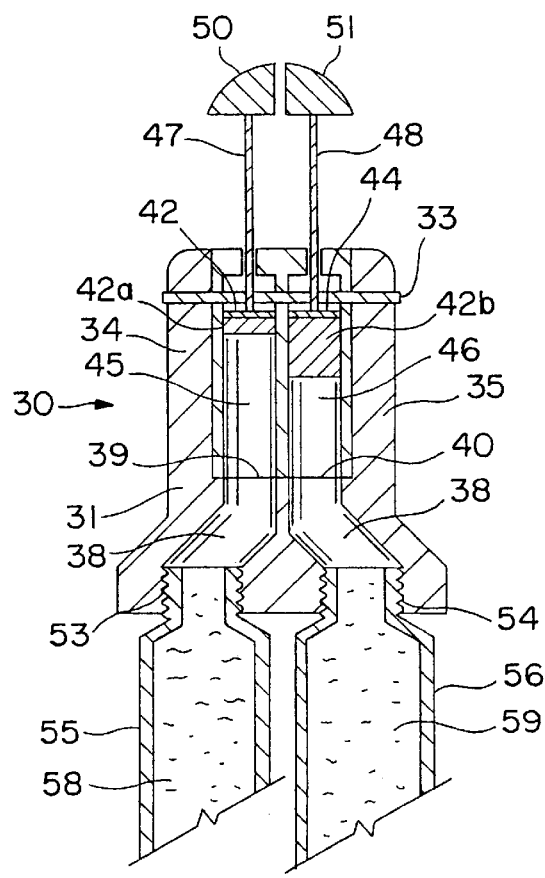
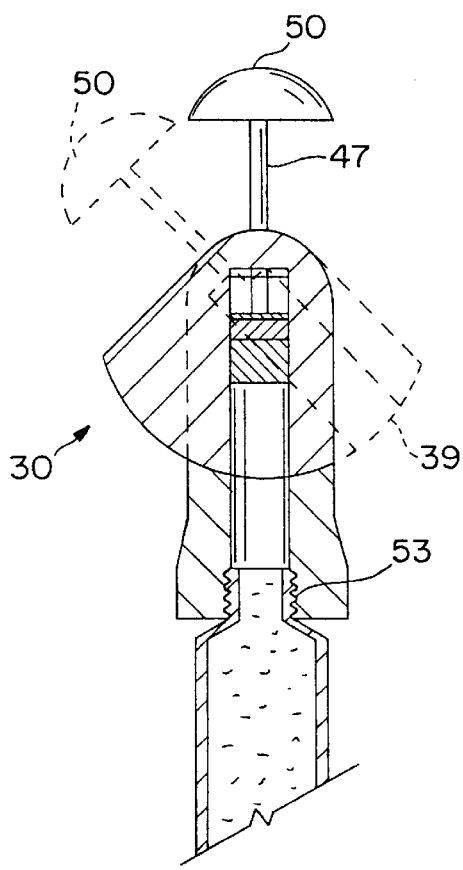
FIG. 2
FIG. 3
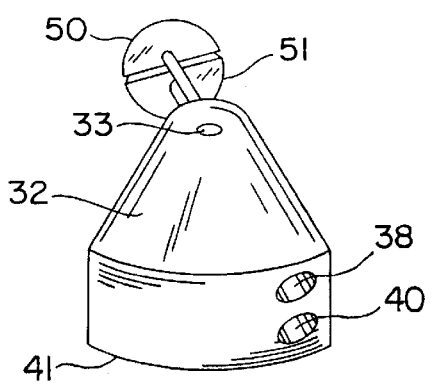
FIG. 3a

HORMONE REPLACEMENT THERAPY METHOD

RELATED APPLICATIONS

This application is a continuation of U.S. patent application Ser. No. 09/288,225 filed Apr. 8, 1999, now U.S. Pat. No. 6,083,528 which is a division of U.S. patent application Ser. No. 08/721,968 filed Sep. 27, 1996, now U.S. Pat. No. 5,922,349 having priority from Provisional Application No. 60/077,182 filed Sep. 27, 1996 which was converted from U.S. patent application Ser. No. 08/535,402, filed Sep. 28, 1995, now abandoned of which U.S. patent application Ser. No. 08/721,968 is a continuation-in-part.

BACKGROUND OF THE INVENTION

This invention relates to a method of conducting hormone replacement therapy (HRT) and to dispensers and kits adapted to practice the method.

HRT in women during the menopausal and post-menopausal period of their lives to prevent or at least diminish the adverse physiological effects thereof, such as bone loss and resultant structural deformation, is now conventional therapy, irrespective of whether the menopause is surgically induced or is the result of the normal aging process. HRT usually involves either the concurrent administration of both an estrogen and a progestogen on a constant, e.g., daily, basis or constant administration of an estrogen and intermittent, e.g., on the 10th to 14th days of a 28 day cycle, administration of the progestogen, at respective dosages which often are changed during the period of HRT, depending on the symptoms currently being displayed by an individual as a result of the menopausal state, the HRT or both. Those doses may be changed infrequently, e.g., every six months or longer at the time the individual visits her doctor for a routine examination, or more often, e.g., from month to month or even more frequently, if the individual is experiencing undesirable menstrual symptoms, e.g., irregular menses, break through bleeding, which is a common consequence of an imbalace of estrogens and progestogens in a continuous combined HRT regimin, excessive blood flow, severe bleeding pain or cramps or a number of other symptoms consistent with the dosage of one or both of the estrogen and the progestogen being too high and thereby creating hormonal side effects, e.g., breast tenderness, nausea, edema, menstrual disorders, etc., or too low and thereby limiting the efficacy of the HRT or creating other side effects. Moreover, because menopause involves a gradual reduction in circulating serum estrogen and progestogen levels, it is usually desirable to initiate HRT during the peri-menopausal period at lower dosages of the estrogen and/or progestogen and gradually increase the dosage thereof as menopause progresses. In addition, a full replacement dosage of estrogens may not be tolerable in a postmenopausal woman whose body has been adapting to estrogen deficiency over a certain period and who may experience breast tension, nausea, oedema and other typical side-effects when receiving the full dosage. In these women, one may wish to start with a very small dosage and increase it only gradually until symptoms have disappeared or plasma levels have reached premenopausal values. Modifying the progesterone dosage level also is frequently necessary during menopause to deal with menses irregularities.

Thus, a fixed combination of an estrogen dosage and a progestogen dosage that is suitable for all menopausal women is impossible to design, for a variety of reasons. One reason is the wide variation from individual to individual in the resorption rate which exists with all modes of administration except intraveneous, which is not practiced in HRT. These differences in bioavailability can reach 100% or more. For example, the bioavailability of estradiol orally averages 5% of the oral dose, which means that in an individual it an be as low as 3% or as high as 6%. Another reason why a fixed combination is not suitable is because of variations in body weight and fat mass proportion, which has an endrocrine function because it contains enzymes to transform hormonal precursors into estrogens. A third reason is the interaction between estrogens and progestogens, i.e., progestogens may only become effective in the presence of estrogens because they stimulate the production of progestogen recepton.

Consequently, estrogens and progestogen which are formulated commercially for HRT typically are sold as combined estrogen/progestogen tablets in more than one dosage strengths. However, the physician is still limited as to the size of the single dose of the estrogen and the progesterone which can be prescribed by those commercially available. Moreover, providing an estrogen/progestogen combination in tablets of multiple strengths adds to the manufacturing cost of producing a combination of a specific estrogen and a specific progestogen and increases significantly the inventory required of pharmacies to make any commercially available combination available to the patients to whom it is prescribed. Therefore, some pharmacies do not stock their estrogen/progestogen products in tablet form in all of the dosage strengths which are commercially available, which can limit the flexibility desired by physicians in a dosage protocol for an individual patient, which ideally is customized in accordance with the symptoms of that patient which are currently manifested by is her.

For the foregoing reasons, there is a need in HRT for a method of administering successive doses of a specific estrogen and a specific progestogen whereby the dosage of either or both can readily be changed by the attending physician or even, if desired by the physician, by the patient, without the necessity of either the patient physically altering the physical form of that daily dosage, e.g., by cutting a tablet into segments, or the doctor prescribing a different form thereof, e.g., tablets of one or both of the hormones in higher or lower strengths. There is also a need for an HRT method which does not require the manufacturer to produce a plurality of products of different strengths in order to practice the method.

There is a further need for a method of self-administering the hormones during HRT by which the individual doses of the estrogen and the progestogen can easily and inexpensively and accurately be altered separately or simultaneously at various times during long term HRT without changing the prescribed dosage form for that patient.

There also is a need for a dispenser of the hormones which are prescribed and a kit comprising the dispenser for the HRT which permit the strength of the individual doses of the estrogen, of the progestogen or of both to be altered as frequently as and to the precise degree which the attending physician deems desirable.

The method of this invention meets these needs by employing in HRT a specific estrogen and a specific progestogen contained in separate extrudable pharmaceutical compositions and administering the compositions concurrently, i.e., either simultaneously as a mixture or in succession as separate extrudates.

The dispensers and kits of this invention meet these needs by dispensing the extrudable pharmaceutical compositions in metered or measured extruded segments.

There are a number of prior patents which disclose devices for dispensing a plurality of flowable materials, i.e., an extrudable solid or a viscous liquid. For a review of that art, see U.S. Pat. No. 5,020,694 and the references cited therein. See also U.S. Pat. Nos. 4,334,787, 4,687,663, 4,826,048, 4,838,457, 5,152,432, 5,240,146 and 5,339,990. Some of these, e.g., U.S. Pat. Nos. 4,240,146, 4,838,457 and 4,826,048, disclose dispensers which comprise means for varying the ratio and/or the quantity of the respective flowable materials which are dispensed in a single dispensing manipulator of the device. In U.S. Pat. No. 5,240,146, both the dosage of two separate injectable pharmaceutical compositions and the ratio thereof can be varied.

None of the prior art devices are directed specifically to the HRT method of this invention which involves, inter alia, one or more of transdermal administration, dosage and estrogen/progestogen ratio regulation and control; administration of the estrogen and the progestogen as extrudable semi-solids; a device or kit for administration of the estrogen and the progestogen which is simple and preferably contains a safeguard against the wrong dose of estrogen or progestogen or ratio thereof inadvertently being self-administered.

OBJECTS OF THE INVENTION

An object of the invention is to provide an HRT method of administering a combination of an estrogen and a progestogen in which the dosage of the estrogen or of the progestogen or of both can readily be changed periodically without the necessity of changing the prescribed form of the pharmaceutical composition.

Another object is to provide such a method in which the size of the dosage of only the estrogen or of only the progestogen or of both is changed only by the attending physician.

A further object is to provide such a method in which the size of the dosage of the estrogen only or of the progestogen only or patient to whom the hormones are prescribed, pursuant to instructions from her attending physician.

A further object is to provide such a method which permits a gradual approach to finding the lowest effective HRT dosage.

A further object is to provide a dispenser whereby the initial individual dose of either the estrogen of the progestogen employed in the methods of this invention or of both can readily and reliably be adjusted to any desired level and that dose can be increased or decreased by necessity of the physician prescribing a different commercial form thereof.

A further object is to provide such a method which permits an individual adjustment of the dosages of the estrogen and progestogen and which assures at the same time a concomitant use of both, similar to a fixed combination product. Thus, it provides the freedom of individual dosage and the reliability of compliance that can be achieved with a fixed combination.

A further object is to provide a dispenser whereby the initial individual dose of either the estrogen or of the progestogen employed in the methods of this invention or of both can readily and reliably be adjusted to any desired level and that dose can be increased or decreased by the attending physician or by the dispensing pharmacist by any amount desired by the physician without the necessity of the physician prescribing a different commercial form thereof.

Yet another object is to provide such a dispenser whereby such a change in the individual doses of either the estrogen or of the progestogen employed in the method of this invention or both can be readily and reliably be changed, either by the physician only or by the patient to whom the hormones are prescribed pursuant to instructions from her attending physician.

Still another object is to provide a kit by which one or more of the foregoing objects can be facilitated.

Other objects will be apparent to those skilled in the art to which this invention pertains.

SUMMARY OF THE INVENTION

In a method aspect, this invention relates to an HRT method of self-administration by a human female of successive doses of an estrogen and of a progestogen, wherein the female dispenses and self-administers successive individual doses of the estrogen and of the progestogen over a protracted period of time, during which period of time at least one of which doses is changed at least once, which method comprises the steps of:

a) dispensing to a delivery surface, from a first source of a first semisolid or viscous liquid pharmaceutically acceptable composition containing a plurality of non-discrete doses of the estrogen, a metered volume of the first composition as a single dose of the estrogen;

b) concurrently dispensing to the delivery surface, from a second source of a second semisolid or viscous liquid pharmaceutically acceptable composition containing a plurality of non-discrete doses of the progestogen, a metered volume of the second composition as a single dose of the progestogen;

c) transporting the metered volumes of the first and second compositions and the delivery surface concurrently to the site of administration of the estrogen and progestogen and administering the dispensed doses of estrogen and progestogen thereat;

d) repeating steps a)–c) on a predetermined schedule; and e) periodically, in response to the physiological symptoms associated with menopause or the HRT currently exhibited by the female, changing the metered volume of at least one of the first and second compositions which are dispensed to the delivery surface as a single dose thereof.

In an article of manufacture aspect, this invention relates to a dispenser adapted for dispensing and self-administering a plurality of successive individual doses of an estrogen and a progestogen from a dispenser containing multiple doses of thereof in separate extrudable pharmaceutically acceptable compositions, in metered single dosage amounts which can simply and accurately be varied by mechanically modifying the dispenser, which comprises:

a) a first container comprising:
(i) a first chamber containing a plurality of doses of the estrogen in a first extrudable semi-solid or viscous liquid pharmaceutically acceptable composition;
(ii) a discharge port through which a volume of the first pharmaceutical composition in the first chamber can be discharged therefrom when discharging pressure is applied to the first container;
(iii) means for applying discharging pressure to the first chamber;

b) a second container comprising:
(i) a second chamber containing a plurality of doses of the progestogen in a second extrudable semi-solid or viscous liquid pharmaceutically acceptable composition;
(ii) a discharge port through which a volume of the second extrudable pharmaceutical composition in the second chamber can be discharged therefrom when discharging pressure is applied to the second container;

(iii) means for applying discharging pressure to the second chamber;

c) a first metering means adapted to receive a volume of the first extrudable pharmaceutical composition extruded thereinto from the first chamber and digitally reciprocally convertible from a receiving mode, where it communicates with the first chamber through the first port and can be filled with a predetermined volume of the first extrudable pharmaceutical composition, to a discharging mode, where a volume of the first extrudable pharmaceutical composition therein can be discharged therefrom and dispensed from the dispenser, which first metering means comprises:

(i) a first adjusting means for varying the volume of the first extrudable pharmaceutical composition which can be extruded into the first metering means a single dose of the estrogen;

d) a second metering means adapted to receive a volume of the second extrudable pharmaceutical composition extruded thereinto from the second chamber and digitally reciprocally convertible from a receiving mode, where it communicates with the second chamber through the second port and can be filled with a volume of the second extrudable pharmaceutical composition, to a discharging mode, where a volume of the second extrudable pharmaceutical composition therein can be discharged therefrom and dispensed from the dispenser, which second metering means comprises:

(i) a second adjusting means for varying the volume of the second extrudable pharmaceutical composition which can be extruded thereinto as a single dose of the progestogen; and e) dispensing means for dispensing from the dispenser, as a single dose of the estrogen and the progestogen, a volume of the first pharmaceutical composition and a volume of the second pharmaceutical composition from the first and second metering means, respectively.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 2 is a cross-sectional front elevation view of a first alternative embodiment of an ointment or creme dispenser in accordance with the present invention;

FIG. 3 is a cross-sectional side elevation view of the first alternative embodiment shown in FIG. 2;

FIG. 3a is a perspective view of a valve member utilized with the embodiment of FIGS. 2 and 3;

DETAILED DESCRIPTION

Figure 1:
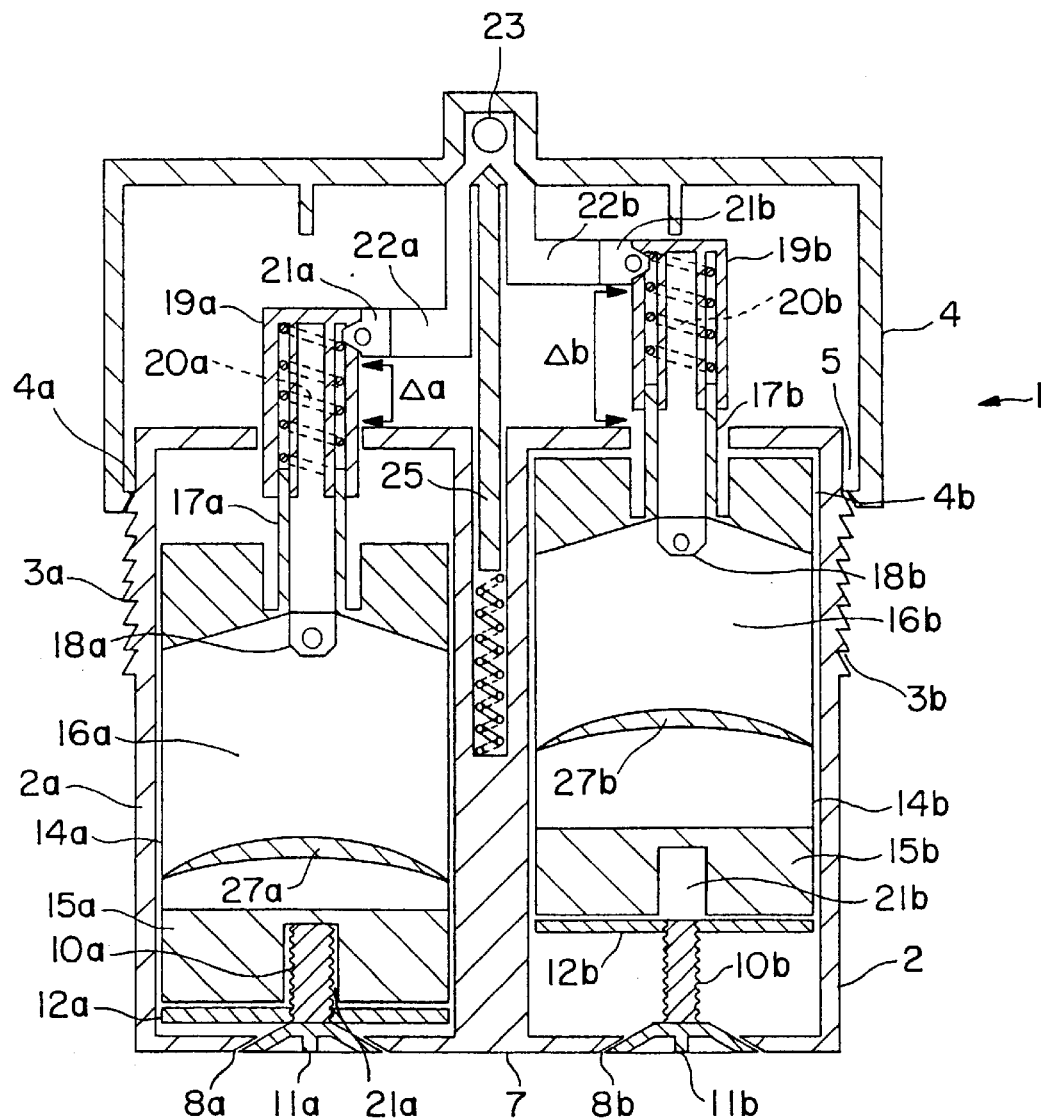
FIG. 1 is a cross-sectional schematic front elevation view of an ointment or creme dispenser in accordance with the present invention.

As used herein, the terms "menopause" and "menopausal" include both the perimenopausal and post-menopausal states; "metered" means measured visually or predetermined mechanically; "concurrently" means simultaneously or in immediate succession; "successive doses" means doses which are administered at periodical spaced intervals, usually daily; "protracted period of time" means longer than a month and includes periods of from several months to several years; "delivery surface" means a surface adapted for administering a single dose and onto which a single dose of the pharmaceutically acceptable compositions are dispensed and which is used to transport the single doses to site of administration thereof; "site of administration" means the area of the body where an HRT pharmaceutical composition is administered e.g., an area of the skin or other topical area, when the pharmaceutical composition is adapted for topical administration, or rectal or vaginal cavity, when the pharmaceutical composition is adapted for oral or rectal or vaginal administration; "flowable" means dispensable in non-discrete form; "non-discrete" means non-particulate"; "spreadable" means administerable by rubbing onto the skin, in a manner similar to a stick deodorant; "extrudable" means dispensable by mechanical force from a multiple dose source thereof as an extrudate having a defined physical conformation for at least the period between when it is dispensed and when it is transferred to a delivery surface; a "rigid extrudate" means one which has a stable physical conformation; a "flowable extrudate" means one which has an unstable physical conformation, i.e., which flattens at a perceptible rate under the influence of gravity; and "sheet" includes films, woven and non-woven fabrics and paper.

In its broadest aspect, the method of this invention employs:
- (a) a first source of a first extrudable pharmaceutical composition containing multiple non-discrete doses of the estrogen which is dispensable therefrom as successively metered single doses;
- (b) a second source of a second extrudable pharmaceutical composition containing multiple non-discrete doses of the progestogen which is dispensable therefrom as successively metered single doses;
- (c) a delivery surface for simultaneously transporting metered amounts of the first and second compositions to a site of administration to which the compositions are adapted for administration from the respective sources thereof;
- (d) means for dispensing successive amounts of the first and second compositions from the respective sources thereof to the delivery surface as single doses of the hormones therein;
- (e) means for metering the amount of the first composition which is dispensed from the first source as a single dose of the estrogen; and
- (f) means for metering the amount of the second composition which is dispensed from the second source as a single dose of the progestogen;

In various embodiments of this invention:
- a. the successive doses are daily doses;
- b. the pharmaceutical compositions are semi-solids which are extrudable as rigid extrudates or viscous liquids which are extrudable as flowable extrudates;
- c. the pharmaceutical compositions are adapted for transdermal administration, which preferably contain a transdermal absorption enhancing agent and they are adapted to be administered by rubbing into the skin or by applying the pharmaceutical compositions to a face of a skin patch which has an adhesive surface and then adhering the patch to the skin of the patient;
- d. the pharmaceutical compositions are adapted for oral ingestion and (i) the pharmaceutical compositions are viscous liquids and the delivery means is a utensil adapted to be inserted into the mouth of the female or (ii) the pharmaceutical compositions are non-sticky semi-solids and the delivery means is a hand of the female;
- e. the pharmaceutical compositions are dispensed by a manually operated pump;
- f. the first and second sources of the pharmaceutical compositions are separate compartments of a unitary dispenser from which individual doses of each pharmaceutical composition are extruded therefrom concurrently, either as two separate exudates or preferably as a single mixed extrudate;
- g. the first and second sources each are contained in a container adapted to be opened by the attending physician for the purpose of altering the size of the individual doses of only one or of both of the estrogen and the progestogen;
- h. the delivery surface is the female's hand and the estrogen and progestogen are administered to the female by rubbing the dispensed compositions onto the area of the skin where transdermal administration of the hormones is to occur;
- i. the delivery surface is a sheet and the hormone-containing compositions are transferred to the skin of the female by applying thereto the face of the sheet bearing the doses of the estrogen and the progestogen, which face optionally also comprises either or both of (i) indicia which identify the respective dosages of the estrogen and progestogen which are contained in the amount of extrudate applied to that face and (ii) an adhesive area surrounding the area to which the extrudate or extrudates are applied which is adapted for adhering the sheet to the skin of the female;
- j. the metered amounts of the pharmaceutical compositions are dispensed from a dispenser housing them in the first and second containers, which dispenser comprises mechanical means for changing the volume of the pharmaceutical composition which is dispensed from one or both of the containers as a single dose, which means preferably does so by altering the volume of the pharmaceutical composition which is dispensed from the first or the second container by changing either the length or the diameter of the composition containing the estrogen or containing the progestogen which is extruded from the dispenser as a single dose;
- k. the schedule of administration of the single doses is daily; the pharmaceutical compositions are semi-solids or viscous liquids; the pharmaceutical compositions are metered from a dispenser in which the first and second containers both are housed in separate chambers, the dispenser comprises mechanical means for changing the volume of the pharmaceutical composition which is dispensed from one or both of the containers in response to manually induced dispensing pressure.

In its various aspects, an article of manufacture of this invention may comprise one or more of the following:
- a. a delivery surface which is a sheet bearing instructions on a face thereof for applying selected amounts of the first and second pharmaceutical compositions, thereon, which sheet optionally comprises visual indicia printed on a face of the sheet which indicate the amount of each pharmaceutical composition which is to be applied to the sheet, the first and second compositions each are adapted for transdermal adsorption of the hormone therein when the compositions are applied to the skin;
- b. a dispenser containing semi-solid first and second compositions;
- c. a dispenser from which the first and second compositions therein are dispensed therefrom simultaneously;
- d. a dispenser from which the first and second compositions therein are dispensed therefrom as a mixed extrudate;
- e. a dispenser which has a pair of storage chambers, each of which contains a pharmaceutical composition which is adapted for topical administration, e., an extrudable semi-solid or viscous liquid or a spreadable stick, and one of which contains multiple non-discrete doses of an estrogen and the other contains multiple non-discrete doses of a progestogen, each of which chambers comprise an outlet port for discharging therefrom the pharmaceutical composition therein and means for applying extruding pressure to the chamber;
- f. a dispenser as described in e), above, in which the storage chambers are tubes which are removable from the dispenser;
- g. a dispenser as described in e), above, each of whose storage chambers or a cap therefor has a metering chamber associated therewith for receiving a predetermined volume of the pharmaceutical composition discharged from the storage chamber;

h. a dispenser as described in e), f) or g), above, which comprises means for changing the volume of the metering chamber into which pharmaceutical composition is dispensed from the storage chamber thereinto as a single dosage of the hormone contained in the pharmaceutical composition;

i. a dispenser as described in e), f) or g), above, whose metering means comprise a pair of extrusion dies mounted on the discharge ends of the storage chambers, which dies determine the diameter of the extrudates discharged from the dispensing means and thus the ratio of the estrogen to the dose of the progestogen in the extrudates which are extruded as a single dose;

j. a dispenser as described in e), f) or g), above, whose metering means comprise a pair of metering conduit or chambers whose length or depth determine the volume of the pharmaceutical compositions discharged from the storage chambers as single dosages of the estrogen and progestogen therein;

k. a dispenser means described in any of e) to i), above, in which the metered volume of the pharmaceutical composition discharged from a storage chamber can be adjusted:

l. a dispenser as described in any of a) to d), above, wherein the metering means is adjustable and the points of adjustment thereof are identified by a series of indicia associated with the metering means which are successively individually visible as the extrusion die is adjusted and which correlate the amount of pharmaceutical composition which determined by the point of adjustment is extruded when a volume thereof is extruded through the die;

m. a dispenser as described in any of a) to l), above, wherein the pharmaceutical compositions are viscous flowable liquids and the first and second metering means comprise a pair of pumps which are connected to the first and second containers, each of which is adapted when activated to first transfer a portion of the viscous liquid composition from the container to which the pump is connected to a metering chamber and then to discharge the metered portion from the metering chamber and from the dispenser;

n. a kit which comprises a dispenser as described in any of a) to f), above, and, as a second component, a sheet as the delivery surface;

o. a kit as described in m), above, and which has as the metering means a series of indicia on the sheet used as the delivering surface;

p. a kit comprising a dispenser as described in any of b) to l), above, which comprises a plurality of means for altering the volume of the conduit or chamber into which the pharmaceutical compositions in the dispenser are discharged for metering a single dose thereof; and wherein one of those means are mounted in or on the dispenser;

q. a kit comprising a dispenser as described in any of a) to l), above, and as a delivery surface, a sheet in the form of a skin patch with adhesive on a face thereof adapted to receive first and second compositions dispensed from the dispenser and which is adapted to be applied adhesively to the skin after the first and second compositions are applied thereto to deliver the hormones therein transdermally.

r. a kit comprising a dispenser as described in any of e) to h), j) and k) above, wherein the pharmaceutical compositions are in stick form and mounted in the dispenser in lipstick-type containers and dispensible therefrom by twisting of the base of the container, which containers preferably are removable therefrom for replacement when empty and the first and second metering means are chambers in a cap for the dispenser which limits the length of the sticks of pharmaceutical composition which can be discharged from the dispenser when the cap is mounted on the dispenser and thus the size of the single doses dispensed therefrom.

The Estrogen and Progestogen

The pharmaceutical compositions employed in the methods present in the article of manufactures of this invention comprise an estrogen and progestogen.

Examples of estrogens which can be employed in this invention (dosages shown are oral; transdermal dosages will vary therefrom in accordance with the adsorption efficacy of the vehicle employed are ethinyl estradiol and mestranol (5–15 mcg/day), estradiol and their esters, e.g., valerate, acetate, benzoate and undecylate (0.5–4 mg/day), estriol, estriol succinate, polyestriol phosphate (2–8 mg), estrone, estrone sulfate and conjugated estrogens (0.3–1.2 mg/day). Of these, ethinyl estradiol, conjugated estrogens, estrone and especially 17β-estradiol are preferred.

Examples of progestogen which can be employed in this invention (dosages are shown; transdermal dosages will vary therefrom in accordance with the adsorption efficacy of the vehicle employed) are micronized
progesterone (100–200 mg/day)
norethisterone acetate (0.5–2 mg/day)
norgestrel (80–250 mcg)
levonorgestrel (40–125 mcg)
gestodene (20–80 mcg)
CPA (1–2 mg)
chlormadinone acetat (1–2 mg)
drospirorenone (1–3 mg)
3-ketodesogestrel (40–120 mcg)

The pharmaceutical compositions of this invention contain, for example, 17β-estradiol in a 2% concentration or levonorgestrel, for example, in a 1% concentration or a biologically equivalent concentration of another estrogen or gestagen, respectively. Amounts of 0.25–1 g of each of the compositions would be sufficient to ensure the release and absorption of minimum daily therapeutic amounts approximately equal to 50 mcg of 17α-estradiol and approximately 40 mcg of levonorgestrel.

The Pharmaceutical Compositions

The pharmaceutical compositions employed in the method of this invention and present in the dispensers of this invention contain the multiple doses of the estrogen or the gestagen in non-discreet form so that individual doses of any desired size can be dispensed therefrom, i.e., they are an extrudable viscous liquid, e.g., one which will flow after being transferred to the delivery surface, or an extrudable semi-solid, e.g., a gel, ointment or creme which is dimensionally stable on the delivery surface, during the period between extrusion and application to the sldn, or a spreadable solid, similar to a stick deodorant. When the composition is a viscous liquid, it preferably has a viscosity of 2,000–100,000 cps, more preferably 5,000–50,000 cps, so that it can be dispensed by a lotion-type pump dispenser and administered by spreading onto the skin by rubbing (topical administration. When the composition is a semisolid it preferably has a viscosity of 50,000–500,000 cps so that it can be extrudated as a pasty mass and administered by either the oral or transdermal route. The compositions preferably have micropenetraton values of less than 1000 mm×10$^{-1}$, preferably more than 1000 mm×10$^{-1}$. Measured by another method (extensometer test) the extensometer values are in the range of from 200 mm$^2$ (more viscous) to 4000 mm$^2$ (more fluid), preferably more than 4000 mm$^{2\cdot}$ As will be appreciated by those skilled in the art, there is no clear distinction between a very viscous extrudable liquid and a very soft extrudable semi-solid. For the purposes of this invention, they are both suitable.

The vehicle in which the estrogen or progestogen is dissolved or suspended can be aqueous, if the selected hormone therein is storage-stable, or nonaqueous, e.g., ethanol or methanol, and can contain one or more of the pharmaceutical carriers, adjuvants or excipients conventionally employed in a composition adapted for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable adjuvants are water, liquid glyceryl triesters with low molecular weight fatty acids or wax-like esters, lower alkanols, natural oils such as corn oil, groundnut oil, sesame oil, castor oil or condensation products thereof with ethylene oxide, and the like, hydrocarbons such as pharmaceutical grade mineral oil, silicones, emulsifiers such as monoglycerides or diglycerides of fatty acids, phospholipic acid derivatives such as lecithin or cephalin, polyalkylene glycols such as polyethylene glycol, aqueous phases to which a swelling agent such as sodium carboxymethylcellulose, sodium alginate, polyvinylpyrrolidone, etc., has been added and to which, in addition, dispersion agents or emulsifiers such as lecithin may be added, polyoxyethylene-derivatives and the like. The adjuvants may, in addition, contain additives such as preservatives, stabilizers, wetting agents, emulsifiers, etc. The composition preferably also contains a transdermal absorption enhancing agent, which can also serve as a carrier component. When the composition is a semi-solid, a conventional extrusion assist agent which reduces the energy required to extrude the composition preferably is present.

Although this invention employs, in a preferred embodiment, a pharmaceutical composition adapted for HRT transdermal self-administration of an estrogen and a progestogen, it will be apparent to those skilled in the art that the principle upon which this invention is based, viz., the use of pharmaceutical compositions containing a plurality of doses of an estrogen and a progestogen in non-unitary dosage form, i.e., an extrudable semi-solid or a viscous liquid as opposed to a tablet, pill, dragee or transdermal patch containing a single dose of the estrogen and of progestogen, in combination with a dispensing means whereby the individual dosage of each of the hormones and preferably also the ratio thereof can be varied by making an adjustment in the dispensing means, can be used in oral therapy by use of an appropriate vehicle for the hormones which is adapted for ingestion and a transport composition suitable for introduction into the mouth, e.g., a spoon with volume indicia for measuring the doses.

Topical Compositions

The pharmaceutical compositions employed in the method of this invention and in the dispensers of this invention are preferably administered by application to an appropriate area of the skin (or mucosa). Therefore they preferably contain an effective amount of an absorption enhancing agent.

The term "topical" as used herein embraces both transdermal and transmucosal administration.

The term "effective" amount when used herein with respect to a topical absorption (or permeation) enhancing agent means an amount that effects a significant increase in the permeability of the area of the skin or mucosa to which the pharmaceutical compositions of this invention are applied and, correspondingly, the desired depth of penetration, rate of administration, and amount of drug delivered systemically.

Examples of absorption enhancing agents are those described in is PCT/US90/01469, viz., a mixture having as a first ether component a diethylene glycol monoethyl or monomethyl ether, or both, e.g., the commercially available product Transcutol, and as a second ester component a compound of the formula $[CH_3(CH_2)_m COO]_n R$ wherein n is the integer 1 or 2, m is an integer from 10 to 18 and R is a lower alkyl ($C_1$–$C_3$) moiety which may be either unsubstituted or substituted with one or two hydroxyl groups, e.g., an ester component which includes one or two capric, lauric, myristic, palmitic or stearic acid residues and one or more lower alkanol, ethylene glycol and propylene glycol moieties, such as the commercially available material sold as "PGML," which is typically a mixture of propylene glycol monolaurate itself, propylene glycol dilaurate, and either propylene glycol, methyl laurate, or both. The ratio (v/v) of the ether to the ester components in this enhancing agent composition ranges from about 90:10 to about 10:90, more preferably from about 90:10 to about 40:60. The preferred ratio may vary depending on the patient and the device used, which device bears volume-indicating indicia for metering the individual doses of the estrogen and of the progestogen, if the dispensing means lacks a metering means it can be the surfaces of a pair of a pair of applicator balls fitted in dual chamberered "roll-on" applicators, comparable to the deodorant dispensers with single applicator balls which are widely used today, the volume of whose reservoirs below the bottom of the balls determine the volumes of the respective single doses of flowable liquids containing the hormones which are dispensable therefrom while the applicator is held in a vertical position; it can be the upper surface of a dual "stick" screw-type dispenser whose cap contain metering cavities which determine the heights of the respective single doses of a pair of tubes of solid spreadable gels which are dispensable therefrom as single doses of the hormones contained therein when the screw dispensing means are turned until the respective tubes fill the metering cavities in the dispenser cap; or it can be a sheet of paper, a plastic film or woven or non-woven cloth, which bears indicia which correlates the size of the extrudate containing the estrogen or the progestogen or both which is applied thereto to the dose of the hormone(s) contained therein, when the multiple dose source of the extrudate applied thereto lacks a device for metering the size of the individual doses. Preferably, the pharmaceutical composition is adapted for transdermal administration and the delivery surface is a hand of the patient receiving HRT.

When a sheet or film is employed as the delivery surface for transporting the pharmaceutical compositions to the area of the skin selected for transdermal administration of the hormones, the sheet or film can also be used as a transdermal patch to extend the contact time of the compositions with the skin, in which case the face of the sheet or film bearing the extrudate(s) thereon preferably also has thereon, alone the periphery of the area bearing the extrudate(s), a strip of adhesive. When the mode of administration is oral, the delivery surface can be edible, such as a sheet of rice paper, or gelatin film so that the delivery surface as well as the extrudate(s) thereon is ingested by the patient. This is useful when the extrudate is a viscous liquid or a sticky semi-solid.

The Site of Administration

The site of administration will, of course, be determined by the nature of the pharmaceutical compositions containing the estrogen or the progestogen, which can be adapted for oral, transdermal or transmucosal administration. Transdermal Administration is preferred.

The Delivery Surface

The delivery (administration) surface can be the patient's own hand, in the case of a spreadable pharmaceutical composition adapted for transdermal or mucosal administration or in the case of a semi-solid pharmaceutical composition adapted for oral ingestion, or if the pharmaceutical composition is a flowable liquid adapted for ingestion; it can be a utensil, such as a spoon, adapted to be inserted into the mouth of the patient, which bears volume-indicating indicia for metering the individual doses of the estrogen and of the progestogen, if the dispensing means lacks a metering means; it can be the surfaces of a pair of a pair of applicator balls fitted in dual chamberered "roll-on" applicators, comparable to the deodorant dispensers with single applicator balls which are widely used today, the volume of whose reservoirs, below the bottom of the balls determine the volumes of the respective single doses of flowable liquids containing the hormones which are dispensable therefrom while the applicator is held in a vertical position; it can be the upper surface of a dual "stick" screw-type dispenser whose cap contain metering cavities which determine the heights of the respective single doses of a pair of tubes of solid spreadable gels which are dispensable therefrom as single doses of the hormones contained therein when the screw dispensing means are turned until the respective tubes fill the metering cavities in the dispenser cap; or it can be a sheet of paper, a plastic film or woven or non-woven cloth, which bears indicia which correlates the size of the extrudate containing the estrogen or the progestogen or both which is applied thereto to the dose of the hormone(s) contained therein, when the multiple dose source of the extrudate applied thereto lacks a device for metering the size of the individual doses. Preferably, the pharmaceutical composition is adapted for transdermal administration and the delivery surface is a hand of the patient receiving HRT.

When a sheet or film is employed as the delivery surface for transporting the pharmaceutical compositions to the area of the skin selected for transdermal administration of the hormones, the sheet or film can also be used as a transdermal patch to extend the contact time of the compositions with the skin, in which case the face of the sheet or film bearing the extrudate(s) thereon preferably also has thereon, alone the periphery of the area bearing the extrudate(s), a strip of adhesive. When the mode of administration is oral, the delivery surface can be edible, such as a sheet of rice paper, or gelatin film so that the delivery surface as well as the extrudate(s) thereon is ingested by the patient. This is useful when the extrudate is a viscous liquid or a sticky semi-solid.

The delivery surface can also be the applicator surface of a stick-type dispenser from which single doses of the estrogen and the progestogen have been discharged from the interior of the dispenser, e.g., by rotating lipstick-type holders for pharmaceutical compositions in stick form which contain the estrogen and the progestogen until single doses of the sticks project from that surface, which can be a surface of the body of the dispenser or the surface of a roller applicator mounted above the ends of the sticks.

Frequency and Period of Administration

The estrogen is ordinarily administered at least once daily preferably without interruption and preferably the progestogen also is administered continuously. If it is desired that menses occurs, e.g., during peri-menopause, a sequential addition of the progestogen may be chosen usually for 12–14 days of a 28-day treatment cycle. This can be achieved by providing means to allow a zero dose of the progestogen. A sequential combined regimen of this type may even include a treatment-free interval of 3–7 days in each treatment cycle following sequential withdrawal of the progestogen. Another alternative for inducing menses would be the continuous combined treatment with the Duo-Vario Pump method in a cyclical regimen with a treatment-free interval approximately every 4 weeks of about 3–7 days as is standard regimen in oral contraception. An antiprogestin is effective for inducing menses in a continuous combined treatment with estrogen plus progestogen as described in PCT application US93/01931. The estrogen and progestogen can be administered uninterrupted desired and preselected frequency, e.g., every 20, 30, 60, 90, 120, 150 or 180 days, by additionally administering a menses-inducing amount of the anti-progestin 1, 2 and/or 3 days prior to the desired day of onset of menses. Alternatively, administration of the estrogen or progestogen can be interrupted during or prior to menses, e.g., beginning on day 21–27 of the menstrual cycle and for up to about 6 days thereafter.

Because the method of this invention is HRT, necessarily the individual doses of estrogen and progestogen are administered over a prolonged period of time, i.e., more than one month, usually at least several months and ordinarily for one or more years and often for one or more decades. During that period of time the size of the individual dose of either the estrogen or the progestogen or both is changed at least once and often two or more times, usually stepwise increased in the case of the estrogen until the minimum effective therapeutic dosage is found. Often, it may be decreased again as the patient progresses from peri- to post-menopause because the estrogen dosage to prevent menopausal bone loss is usually lower than the dosage that is needed for effectively treating climacteric complaints.

DESCRIPTION OF SPECIFIC EMBODIMENTS

The First Embodiment (FIG. 1)

A first preferred embodiment of a dispenser of the invention, shown in FIG. 1, is a unitary dual ointment dispenser 1 having a reservoir lower body portion 2 and an upper dispensing cap portion 4 fitted on the upper portion of body portion 2. Body portion 2 consists of a pair of housings 2a and 2b which are joined together and maintained in a spaced apart relationship by a spacer bar 7 which projects upwardly only portion of the height of the housings, thereby leaving a space between the upper portion of the housings which forms a conduit 5 which is closed at its lower end and open at its upper end. As a safety mechanism to ensure that a full single dose is metered into the metering cap portion 4 after a single dose is dispensed from dispenser housings 2a and 2b each have, as an optional feature, a vertical saw toothed strip 3a and 3b on opposing exterior sides thereof which engage an inner lip 4a and 4b on the inner surface of the bottom of upper body portion 4. Contained in the bottom surface of housings 2a and 2b are a pair of orifices 8a and 8b of a size and conformation which permits the threaded shanks 10a and 10b of a pair of adjustment screws 11a and 11b to project respectively through orifices 8a and 8b into the interior of lower portion 2 and permits the heads of screws 11a and 11b to seat flush with the outer surface of the bottom surface of housings 2a and 2b. Positioned interiorly in lower portion 2 and threaded respectively on screws 11a and 11b are a pair of thin support nuts 12a and 12b which provide, respectively, support bases for a pair of cylindrical containers 14a and 14b positioned in housings 2a and 2b and containing respectively, pharmaceutical compositions 16a and 16b in ointment form which contain a plurality of single doses of an estrogen and a progestogen, respectively. Cylindrical containers 14a and 14b have thick bases 15a and 15b, respectively, with a cavity 13a and 13b, respectively, therein projecting upwardly from the exterior surface thereof and adapted to receive the respective threaded ends of adjustment screws 11a and 11b in a sliding fit manner. Forming a seal between bases 15a and 15b and the contents 16a and 16b of containers 14a and 14b is a spacer member 27a and 27b, respectively, which is fitted to slide in an upward direction in the bottom of containers 14a and 14b, respectively, and which maintains the cavity formed between it and the upper surface of the containers filled with the contents thereof as individual doses are dispensed from dispenser 1. Mounted on the respective upper ends of containers 14a and 14b, in fluid communication with the contents thereof by an orifice in the upper end of the container, is a smaller diameter open ended cylindrical extension 17a and 17b, respectively, which is in fluid communication with the contents 16a and 16b of containers 14a and 14b, respectively, via lower check valves 18a and 18b, respectively, which prevent backflow of pharmaceutical compositions 16a and 16b in extensions 17a and 17b into containers 14a and 14b. Slidably mounted on cylindrical extensions 17a and 17b are sleeves 19a and 19b, respectively, which are closed at their upper end and which contain mounted therein a spring 20a and 20b, respectively, which maintains the sleeves 19a and 19b at a maximum distance apart from the lower valves 18a and 18b, but permits the sleeves 19a and 19b to slide over the extensions 17a and 17b, as cap portion 4 is raised and lowered. Extensions 17a and 17b are in fluid communication through upper dispensing valves 21a and 21b, respectively, with flexible dispensing conduits 22a and 22b, respectively, each of which are in common fluid communication with dispensing outlet 23. Positioned between the upper surface of lower body portion 2 and the under surface of upper body portion 4 is a spring 24 which is held in position by guidance bar 25, the upper end of which is mounted on the inner surface of cap portion 44 and slidable mounted in conduit 5. Guidance bar 25 has an enlarged lower end 25a to which the upper end of spring 24 is mounted.

In operation, adjustment screws 11a and 11b are turned in an amount which raises containers 2a and 2b to a height which determines the desired volume of pharmaceutical compositions 16a and 16b which can be transferred from containers 2a and 2b, respectively, into the chambers defined by cylindrical extension 17a and sleeve 19a and cylindrical extension 17b and sleeve 19b, respectively, which volumes determine the respective single doses of progestogen and estrogen dispensed from container 1 which cap 4 is pressed completely downward over lower body portion 2. The adjustment screws 11a and 11b provide meters for measuring and determining the volume of dispensed doses of estrogen and progestogen, respectively.

A single metered dose of a mixture of the pharmaceutical compositions 16a and 16b in containers 14a and 14b is dispensed from dispenser 1 by pressing upper body portion 4 against lower body portion 2. The free spaces $\Delta^a$ and $\Delta^b$ defined by the distances between upper dispensing valves 21a and 21b, respectively, and the upper surface of the top of lower body portion 2 define the distance that sleeves 19a and 19b can be slid downward onto extensions 17a and 17b, respectively, and the distance which containers 14a and 14b have been raised by screws 11a and 11b determines the volume of the pharmaceutical compositions 16a and 16b which can be transferred from containers 14a and 14b into extensions 17a and 17b and from there into sleeves 19a and 19b when cap 4 is pressed downwardly onto base portion 2 of dispenser 1. Lower valves 18a and 18b prevent the thus-transferred compositions from being forced back into containers 14a and 14b and upper valves 21a and 21b permit the thus-transferred compositions to be dispensed through dispensing outlet 23.

Cap 4 is urged back to its metering extended position by spring 24. As it returns to this position, a negative pressure is created in containers 2a and 2b, which causes the compositions therein to be drawn into extensions 17a and 17b, which in turn causes the compositions in the extensions to be drawn into sleeves 19a and 19b thereby filing them once more, and providing a metered single dose of the progestogen and estrogen which can be dispensed when cap 4 is once again pressed down onto lower body portion 2.

In the embodiment shown in FIG. 1, Cap 4 is released from its lowered position on lower body 2 by squeezing the side walls of dispensing cap 4, which disengages lips 4a and 4b from their engagement with saw-toothed strips 3a and 3b on the sides of containers 2a and 2b.

In an alternative embodiment (not shown), a security mechanism to ensure that each dispensed dose is a full dose of both the progestogen and the estrogen, lips 4a and 4b are replaced by spring loaded mounted on and in spaced relationship from the inner surface of the side wall of cap 4 and the upper portion of the side walls of containers 2a and 2b on which saw-toothed ships 3a and 3b are mounted converge toward the upper ends thereof, so that those saw-toothed strips are in a non-parallel relationship with the saw-toothed strips mounted on the inner surface of cap 4 and the former forces the latter into a parallel position, as a result of the latter being spring loaded, as the cap is moved downwardly onto the lower body portion 2 of dispenser 1 to dispense a single dose of the pharmaceutical compositions. The non-parallel relationship of the respective saw-tooth strips permits downward movement of the cap but prevents upward movement until the cap has been pressed downwardly onto lower body portion 2 to the full extent, at which point they disengage and upward movement becomes possible. In a further alternative embodiment (not shown) both the lips 4a and 4b and the saw-toothed strips 3a and 3b are omitted and the dispenser 1 bears instructions that, to ensure that a full single dose is dispensed, the cap should not be released after it is pressed down onto lower body 2 until it is pressed down to the maximum possible extent.

The Second Embodiment (FIGS. 2, 3 and 3a)

Referring now to FIGS. 2 and 3, there is shown a second embodiment of a dispenser of the invention configured as a dual ointment dispenser 30 which includes a dispensing head 31 having a valve body 32, shown in perspective in FIG. 3a, which is pivoted on a pivot pin 33 between two flanges 34 and 35 which are unitary with a base 36. Base 36 has channels 37 and 38 therein which communicate with valve conduits 39 and 40 in an arcuate interface surface 41 of valve body 32 when it is in the solid line position of FIG. 3. When valve body 32 is in the dotted line position of FIG. 3, the open ends of valve conduits 39 and 40 are exposed so that the ointment therein may be dispensed from assembly 30.

Disposed in valve body 32 are a pair of metering and dispensing pistons 42 and 44 which are mounted in cylindrical passage 45 and 46 formed in the valve body 24 and aligned with valve conduits 33 and 34. Pistons 40 and 42 are connected by rods 47 and 48 to a pair of handles 50 and 51 which, when pressed, while valve body 24 is in its dispensing position shown in ghost in FIG. 3, push the pistons down into the cylindrical passages 44 and 46, respectively.

The base 30 of the dispenser has a pair of threaded inlet openings 53 and 54 which receive containerized sources of ointment in the form of ointment tubes 55 and 56 therein. In accordance with the present invention, ointment tube 55 is filled with a progestogen-containing ointment 58 and tube 56 is filled with an estrogen-containing ointment 59 or vica versa. Upon squeezing tube 55, ointment 58 is extruded through the passage 31 into valve conduit 33 in the valve body 24 to load the valve body. In a conventional way, the tube 44 is vented via a small diameter vent (not shown) which is small enough to let air out of the upper end of valve conduit 33 but too small to permit ointment 58 to readily be extruded through it. Similarly, ointment 59 is dispensed from tube 56 by squeezing tube 56 and forcing ointment 59 through passageway 32 in the base 30 into the valve conduit 34 in valve body 24. As is seen in FIGS. 2 and 3, pistons 40 and 42 have plugs 40a and 42a mounted on the respective lower ends thereof, the latter being longer than the former, thereby reducing the internal volume of valve conduit 33 compared to that of valve conduit 34. The pistons 40 and 42 with the plugs 40a and 42a provide meters for measuring and determining the volume of dispensed doses of estrogen and progestogen, respectively. Consequently, less ointment 58 is extruded into valve body 24 when tube 56 is squeezed than ointment 59 when tube 55 is squeezed. These plugs can be changed by removing pin 26, thereby permitting valve body 24 to be disengaged, and replacing the appropriate one of plugs 40a and 42b with another plug of different length which reduces or increases the dosage of the estrogen or progestogen by the desired amount by reducing or increasing the amount of ointment 58 or 59 which can be extruded into conduits 33 and 34, respectively.

In order to dispense a dose with the desired amounts of progestogen and estrogen, the valve body 24, with valve conduits 33 and 34 filled with ointment 58 and 59, respectively, is pivoted about pivot pin 26 to the position shown in ghost in FIG. 3 and the knobs or buttons 50 and 51 are pressed to push the progestogen and estrogen out through the openings 33 and 34 into, for example, the patient's hand where the dual dose can be mixed and then applied.

The Third Embodiment (FIGS. 4–8)

Figure 4:
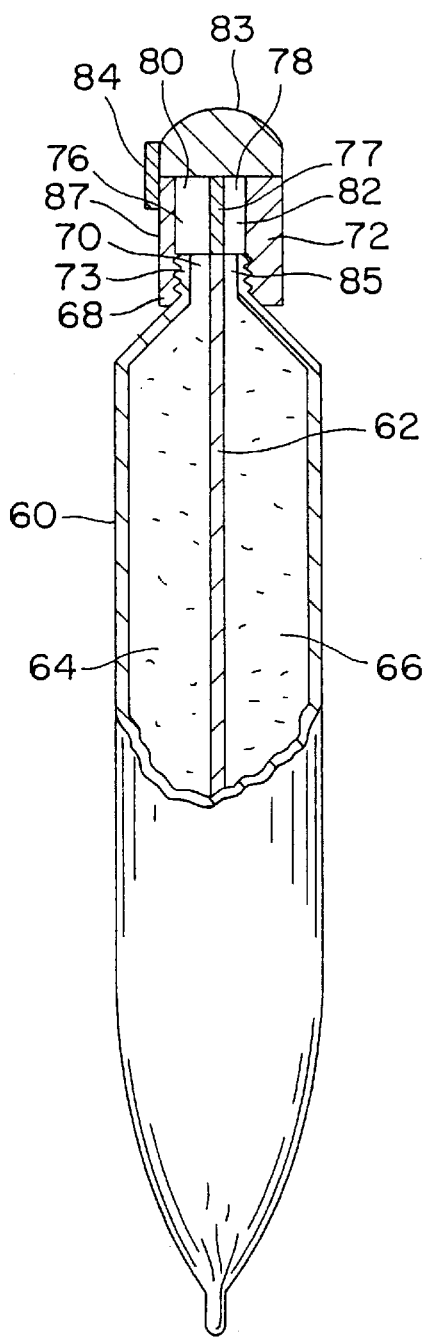
FIG. 4 is a side elevation of a single tube configured in accordance with the the present invention, having a pair of chambers and a metering and dispensing nozzle, adapted for use in a kit which includes metering means for measuring the size of the single doses dispensed therefrom, such as shown in FIG. 9.
Figure 5:
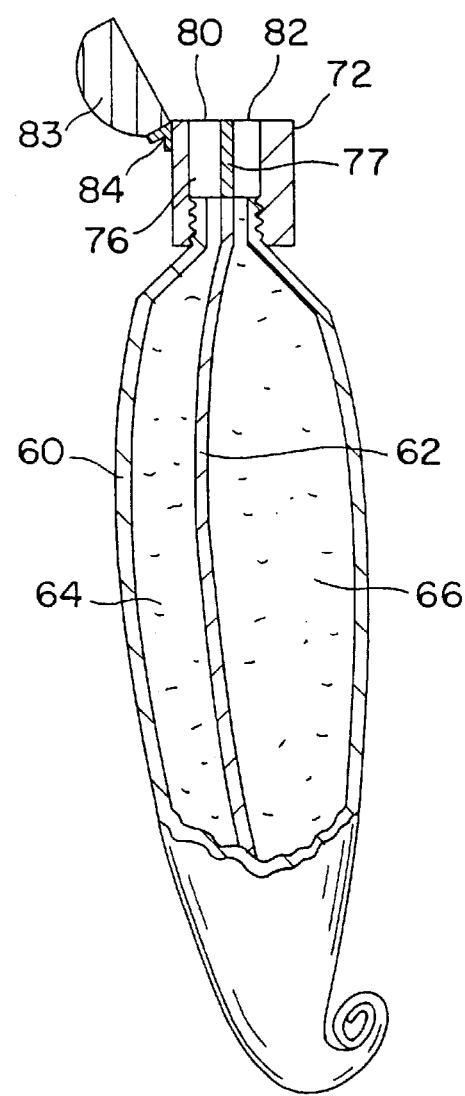
FIG. 5 is a side elevation of a single tube similar to that shown in FIG. 4 but having a differently configured metering and dispensing nozzle and showing the tube partially rolled up from the bottom, in a partially emptied configuration.

In the embodiment of FIGS. 4 and 5, a dual-chambered ointment tube 60 has an interior wall 62 which divides the dual-chambered tube 60 into a first compartment 64 and a second compartment 66 which compartments provide containerized sources of ointment. Dual-chambered ointment tube 60 has a neck 68 with an opening 70 therein through which interior wall 62 extends.

Figures 6, 7, 8:
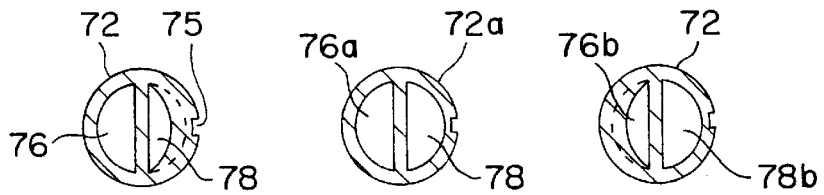
FIG. 6 is a cross-sectional view along line 6—6 of the metering and dispensing nozzle of the embodiment of FIG. 4.
FIG. 7 is a corresponding view of a first alternative embodiment of the metering and dispensing nozzle shown in FIG. 6.
FIG. 8 is a corresponding view along lines 8—8 of FIG. 5 of a second alternative embodiment of the dispensing nozzle shown in FIG. 6.

A dispenser nozzle 72, also shown in FIG. 6, is snap-fitted onto the neck 68 by engagement with an annular rib 73 projecting from neck 68. Dispenser nozzle 72 has a notch 75 thereon which engages a single rib on the threaded neck 68 so that it is always oriented the same with respect to interior wall 62.

Dispenser nozzle 72 has dividing wall 77 aligned with interior wall 62 which forms in dispenser nozzle 72 a divided extrusion die having a first cavity 76 and a second cavity 78 therein which have outlet openings 80 and 82, respectively. Outlet opening 80 has a larger cross-sectional outlet opening 82, as a result of the portion 87 of outer wall of dispenser nozzle 72 defining outlet 80 being thinner than the portion 85 which defines outlet 82. Outlet openings 80 and 82 are closed by a cap 83, shown in closed position in FIG. 4 and in open position in FIG. 5, pivoted on a hinge 84.

Upon rolling up the dual-chambered ointment tube 60 from the bottom in the manner shown in FIG. 5, the ointments contained in compartments 64 and 66 pass through cavities 76 and 78 at different rates and are dispensed from nozzle 72 in different volumes. Accordingly, if cavity 64 is filled with a progestogen-containing composition and cavity 66 is filled with an estrogen-containing composition, a dual dose of different volumes of the two compositions is dispensed. The ratio of estrogen 89 to progestogen 88 in a single dose is varied by simply changing the dispensing nozzle 72 to one having a different wall configuration 72a or 72b, as shown in FIGS. 7 and 8 so that the volumes of the compositions in cavities 76 and 77 are dispensed at a different ratio. For example, by replacing nozzle 72 with nozzle 72a or 72b, shown in FIGS. 7 and 8, respectively, the ratio of progestogen to estrogen in a single dose is increased by a predetermined amount.

Figure 9:
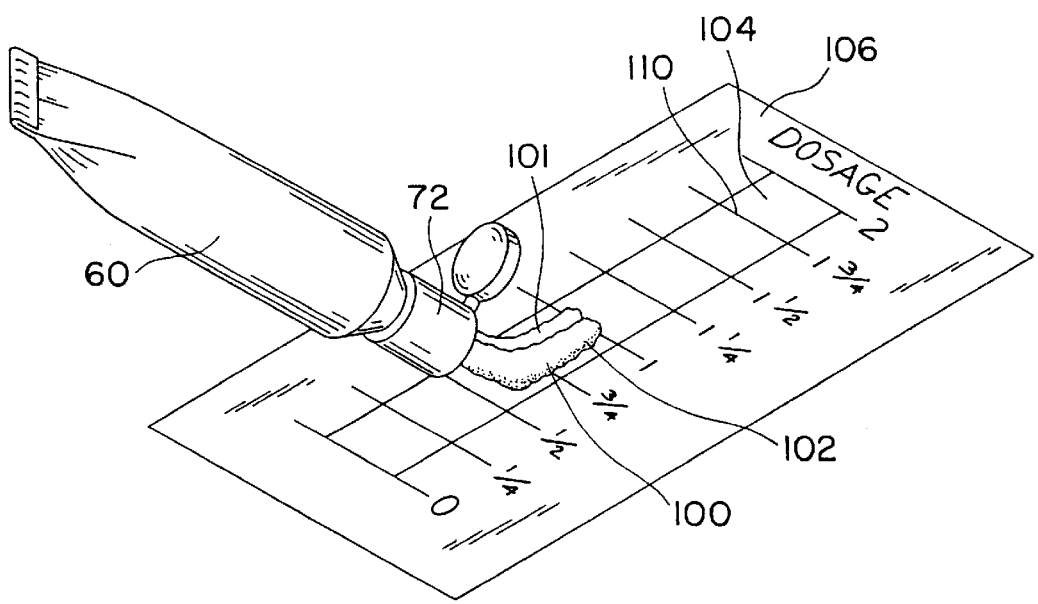
FIG. 9 is a perspective view of another embodiment of a kit of this invention in the form of an ointment tube of the type shown in FIGS. 4 and 5, dispensing a mixture of two ointments, as a single extrudate, onto a chart having a liner graph thereon.

As shown in FIG. 9, the third embodiment is an element of a kit consisting of a delivery sheet 106 and a single dual-compartment dispensing tube 60 of the type shown in FIGS. 4 and 5, containing an estrogen-containing composition 101 in one compartment and a progestogen-containing composition 102 in the other. As in the embodiment shown in FIG. 9, sheet 106 can be one of a plurality of single use sheets in pad form and formed of the same materials as that embodiment. Sheet 106 bears on a face thereof a single graph 104 with linear delineations 110 which identify various single combined doses of the estrogen and the progestogen, e.g., a standard dose, identified by the integer "1", and smaller and larger doses identified by fraction numbers. A combined extrudate 100 of the estrogen-containing composition 101 and the progestogen-containing composition 102 is shown in FIG. 10 being deposited on sheet 106.

A physician prescribes the initial single dose of the estrogen and the progestogen by identifying the length of the extrudate 100 which should be deposited on graph 104 as a single dose. To increase or decrease the dose of both the estrogen and the progestogen while maintaining the ratio thereof constant, in response to one or more symptoms currently being manifested by the patient on HRT, the physician instructs the patient to change the length of the extrudate 100 which is deposited on sheet 106 as a single dose. To change the dose of only the estrogen or only the progestogen in a single dose self-administered by the patient, the dispensing nozzle 72 is replaced by the attending physician, or by the patient, with a nozzle 72a or 72b shown in FIGS. 7 and 8, which changes in an appropriate amount the cross-sectional area of the portion 101 or of 102 of the extrudate which is deposited by the patient on sheet 106.

The nozzles 72, 72a and 72b provide meters for measuring and determining volumes of dispensed doses of estrogen and progestogen, respectively.

Figure 10:
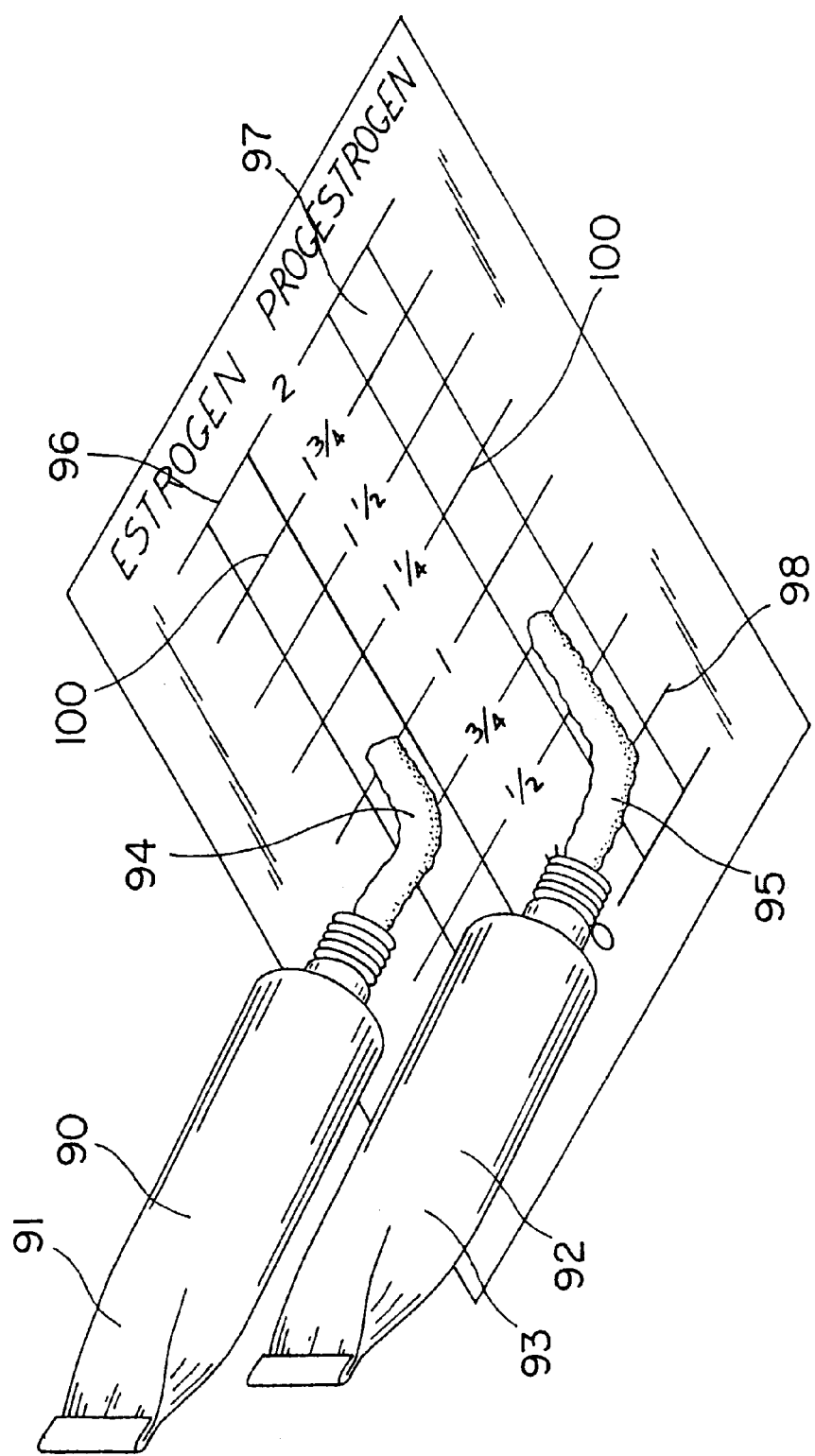
FIG. 10 is a perspective view of a kit of this invention which employs a pair of ointment tubes dispensing separate extrudates of two ointments on a chart having a pair of linear graphs thereon.

The Fourth Embodiment (FIG. 10)

The fourth embodiment shown in FIG. 10 is a kit consisting of a pair of dispensing tubes 90 and 92 and a delivery sheet 98 which dispensing tubes provide containerized sources of estrogen and progestogen ointments. Tube 90 is filled with an estrogen-containing ointment 91 and tube 92 is filled with a progestogen-containing ointment 93 which tubes provides containerized sources of ointment. Sheet 98 can be one of a plurality of single use sheets in a pad and formed of paper or a multiple use single sheet formed of a durable washable material, such as polyethylene, polypropylene or acrylic resin. Sheet 98 bears on a face thereof a pair of graphs 96 and 97 with linear delineations 100 which identify, respectively, various single doses of the estrogen and the progestogen, e.g., a standard dose, identified by the integer "1", and smaller and larger doses identified by fraction numbers. Extrudates 94 and 95 of the estrogen-containing composition 91 contained in tube 90 and of the progestogen-containing composition 93 contained in tube 92 are shown in FIG. 10 being deposited on graphs 96 and 97, respectively. The graphs 96 and 97 define first and second meters, respectively wherein the meters are comprised of first and second arrays of linear markings, respectively. The first and second meters receive and indicate measured volumes of estrogen and progestogen, respectively.

A physician prescribes an initial dose of the estrogen and the progestogen by identifying the length of the extrudate 94 and 95 which should be dispensed by the female to whom the hormones are to be self-administered on graphs 96 and 97, respectively, as a single dose. This identification can be assisted by the physician coloring the appropriate portion of graphs 96 and 97, as shown in crosshatching in FIG. 7. To change that dose, in response to one or more symptoms currently being manifested by the patient HRT, the physician instructs the patient to change the length of one or both of extrudates 94 and 95, so that the amount of one or both of the estrogen and progestogen in a single dose self-administered by the patient is increased or decreased, as deemed appropriate by the physician.

Figure 11:
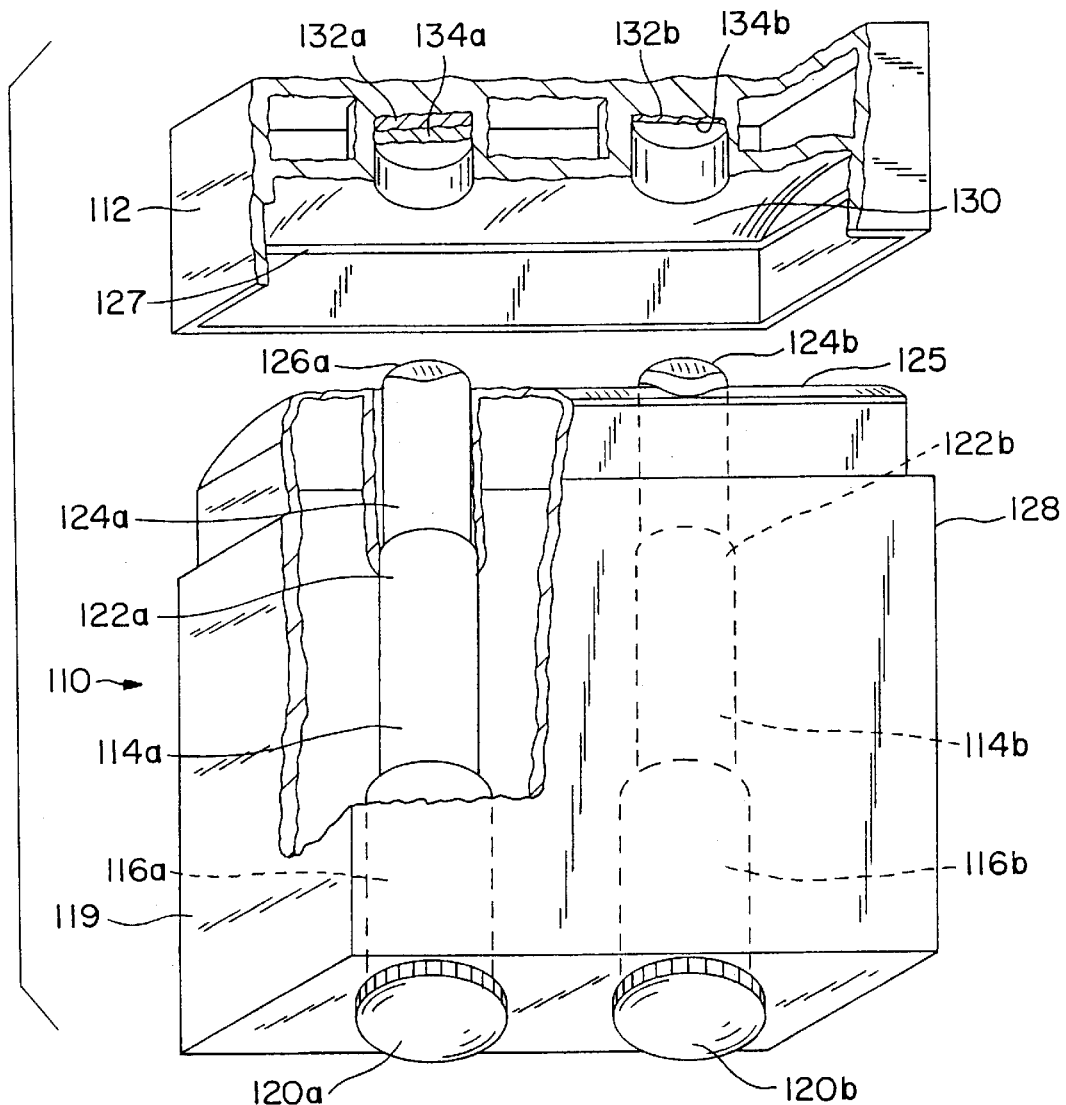
FIG. 11 is an exploded perspective view of a stick-type dispenser and metering cap therefor with the forward wall of each partially removed to show the pair of spreadable stick pharmaceutical compositions housed in rotable lipstick-type housings mounted in the former and the conformation of the metering chambers in the latter.

The Fifth Embodiment (FIG. 11)

The fifth embodiment shown in FIG. 11 is a dual stick-type applicator 110 and metering cap 112. Mounted in the base of applicator 110 are a pair of lipstick-type dispensers 114a and 114b, each of which has a stationary tubular base 116a and 116b, respectively, rigidly but removably fitted into a hole (not shown) in the base wall 119 of applicator 110 which dispensers provide containerized sources of estrogen and progestogen. Rotably mounted in the base of each of the dispensers is a conventional twist-type dispensing knob 120a and 120b, respectively, attached to cylindrical holders 122a and 122b, respectively, for a stick 124a and 124b of a solid spreadable estrogen-containing and progestogen-containing pharmaceutical composition, respectively. Holders 122a and 122b are connected by conventional screw drive mechanism (not shown) to tubular bases 116a and 116b, respectively, so that twisting knobs 120a and 120b will raise (or lower) holders 122a and 122b, respectively, and the sticks of pharmaceutical composition mounted therein so that the ends 126a and 126b, respectively, of the latter project beyond the applicator face 125 of applicator 110 (or are recessed below it).

Cap 112 has a ledged inner surface 127 which permits the cap to be seated on a correspondingly ledged top portion 128 of applicator 110 and a curved upper inner surface 130 which conforms to the applicator surface 125 of applicator 110. In the upper surface 130 are recessed portions 132a and 132b which are aligned with sticks 124a and 124b and which provide cavities which determine, when cap 112 is mounted on applicator 110, the maximum distance beyond the applicator surface 125 that the ends 126a and 126b of sticks 124a and 125b can be dispensed by twisting knobs 120a and 120b, respectively, which thus determines the maximum single dose of estrogen and progestogen that can be dispensed. An insert 134a and 134b mounted in recessed portions 132a and 132b reduces that maximum distance and thus also the size of the single doses.

The inserts 132a and 132b and inserts 134a and 134b in cooperation with the operation of the twist knobs 120a and 120b provide meters for measuring and determining the volumes of dispensed doses of estrogen and progestogen, respectively.

In kit form, cap 112 is provided with a series of inserts, identified by dosage numbers or distinguishing colors, similar to inserts 132a and 132b but of different thickness. The attending physician or dispensing pharmacist inserts the appropriate insert or inserts in recessed portions 132a and 132b which will permit the amounts of sticks 124a and 124b which can be dispensed beyond the surface of applicator surface 125 and thus can be applied to the skin for transdermal administration as a single dose.

Figure 12:
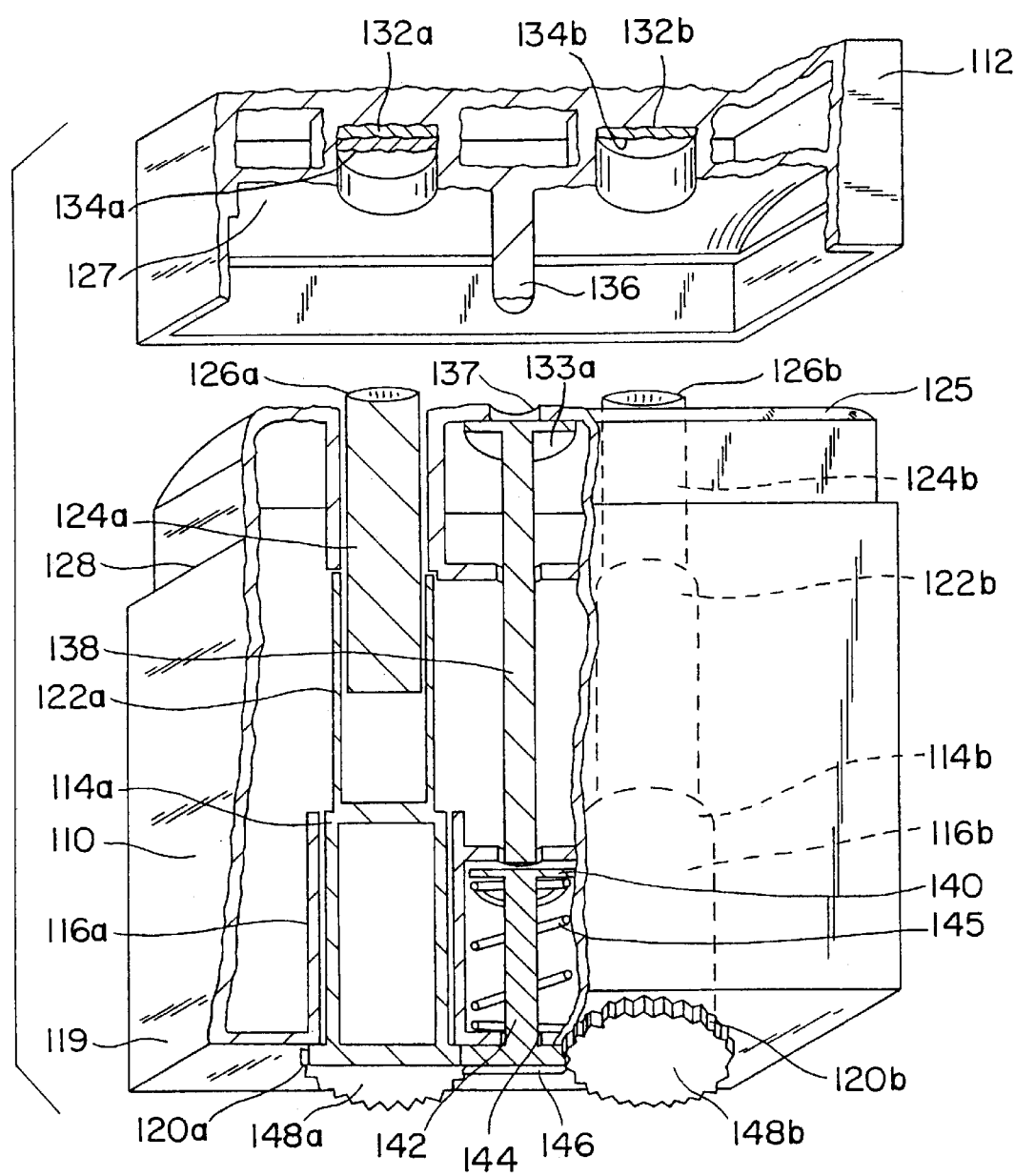
FIG. 12 is a vertical plan view, partially in cross section to show the pair of a dual dispenser and cap, similar to the stick-type embodiment shown in FIG. 11, which also has a lock mechanism which prevents the pharmaceutical compositions from being dispensed therefrom except when the metering cap is mounted on the dispenser.

The Sixth Embodiment (FIG. 12)

The sixth embodiment shown in FIG. 12 also is a dual stick-type applicator 110 and metering cap 112 and the other correspondingly numbered elements which function in the identical manner. Additionally, this embodiment has a security system which prevents sticks 124a and 124b from being dispensed unless the metering cap 112 is mounted on applicator 110, thereby avoiding the possibility of the self-administering female "eyeballing" the amounts 126a and 126b of sticks 124a and 124b dispensed as a single dose. The security system uses a rod 136 mounted on the inner surface of cap 112 soas to project downward toward but above base 119 of applicator 110, between dispensers 114a and 114b, and coaxially with an orifice 137 in the upper surface of applicator 112. Vertically movably mounted within applicator 110, coaxially with rod 136 and between dispensers 114a and 114b, is a second rod 138 having a face plate 138a on the upper end thereof, which contacts the inner surface of the applicator wall 125 and prevents it from projecting through orifice 137. Rod 138 projects downwardly and contacts a base plate 140 coaxially positioned over orifice 144 in the bottom wall of applicator 110. Mounted on the lower face of base plate 140 is a third rod 142 which projects downwardly and projects through orifice 144 flush with the outer surface of bottom wall 119 of applicator 110. Base place 140 is held in an upwardly urging manner against the bottom end of rod 138 and in a first locking position by a spring 142 mounted on and projecting upwardly from the inner surface of the bottom wall 119 of applicator 110 when cap 112 is not seated on applicator 110. Mounted on the lower end of third rod 142 is a locking bar 146 which fits between a pair of the plurality of ribs 148a and 148b in the circumference of knobs 120a and 120b and is urged upwardly by a spring 145 into a first locking position, which prevents the knobs from rotating when cap 112 is not mounted on applicator 110, and which is forced downwardly and projects beyond the ribs into a second non-locking position, which permits the knobs to be rotated, when the cap is mounted on the applicator. The daily doses are dispensed and administered in the same manner as the fifth embodiment shown in FIG. 11 with the inserts 132a and 132b and the inserts 134a and 134b in cooperation with the twist 148a and 148b providing meters for measuring and determining the volumes of dispensed doses of estrogen and progestogen, respectively.

In a variation (not shown) the cap has two positions on which it can be mounted on the applicator, viz., a first capping position which protects the applicator surface 125 when the applicator is not in use and maintains locking bar 146 in its locked position as shown in FIG. 12 (which prevents knobs 120a and 120b from being turned) and a second metering position as described above, which requires the cap to be pressed onto applicator 110 beyond its capping position and forces locking bar 146 beyond ribs 148a and 148b so that knobs 120a and 120b can be turned.

Although the first through fourth embodiments are designed for dispensing the hormone-containing pharmaceutical compositions employed in the method of this invention which are in the form of ointments, it will be apparent to those skilled in the art that they can be adapted for use with more viscous compositions which form rigid, pellet or rod-like extrudates which can be administered orally. As will also be apparent to those skilled in the art to which the invention pertains, the dispensers and kit of this invention can also be used for oral contraception in fertile women, e.g., when it is likely the dosage of only the estrogen or progesterone will be changed or when it is desired to include progesterone in only a selected few days of the menstrual cycle or when it is desired to add an anti-progestogen during selected days thereof while maintaining the estrogen and progestogen dosages unchanged.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, any temperatures are set forth uncorrected in degrees Celsius and unless otherwise indicated, all parts and percentages are by weight. The entire disclosure of all applications, patents and publications, cited above and below are incorporated by reference.

EXAMPLE 1

A 55–60 year old post-menopausal Caucasian female who has, for about 6–12 months, displayed menopausal symptoms which included hot flashes and episodic sweating and in addition has a family history of osteoporosis of her mother and a current estrogen blood serum level below 30 pg/ml, is provided with a hormone dispenser according to FIG. 1 and instructed to dispense daily therefrom a single dose onto her hand and rub the dispensed dose into the washed skin of one of her upper arms.

The two chambers of the dispenser each contain 100 ml of a semi-solid (viscosity 10,000 cps) pharmaceutical composition based on the following vehicle:

| | |
|---|---:|
| Carbopol 980 | 1.0 g (= 1%) |
| NaOH | ca 0.075 mg |
| Benzyl alcohol | 1.0 ml |
| Propylene glycol | 10.0 ml |
| Purified water | ad 100 ml |

The pharmaceutical composition is prepared by mixing the active compound in the benzyl alcohol, propylene glycol and a portion of the water, homogeneously dispersing the Carbopol therein; neutralizing the resulting dispersion with the NaOH and mixing the remainder of the water therewith. The active compound 14a is 200 mg of 17β estradiol. The active compound 14b is 100 mg levonorgestrel. Depressing the upper body portion 4 discharges 0.25 ml from each container to form a 50:50 mixture of the estrogen-containing and of the progestogen-containing pharmaceutical composition which is dispensed through outlet 23 as a single dose onto the patient's hand, who rubs it into the washed skin of one of her upper arms. This procedure is repeated daily.

After 4 weeks, the patient is reexamined for incidence of menopausal symptoms and possible side effects of the hormonal treatment. Upon finding the patient is currently experiencing a lower incidence of menopausal symptoms but not satisfactorily relieved and no significant side effects to the HRT her dispenser is adjusted so that the volume of the estrogen containing pharmaceutical composition which is dispensed as a single dose is increased by 25%, by adjusting the size of the single dose dispensed from dispenser 1, and the volume of the progestogen-contained pharmaceutical composition which is concurrently dispensed remains the same. In case the dose adjustment decision needs further support, the estradiol blood serum level is measured. A blood level of significantly below 60 pg/ml justifies adjusting the estrogen dosage upwardly accordingly. In addition, significant rates of breakthrough bleeding during the time of treatment justifies increasing of the daily dosage of the progestogen, e.g., by increasing the volume of the progestogen-containing pharmaceutical composition by 50%. If the woman still experiences vaginal bleeding after another 4 weeks of treatment, a further dose increase of the progestogen is justified. An endometrial biopsy prior to this decision can guide the physician in finding the right balance between the estrogen dosage and the progestogen dosage as the histologic examination of the biopsy would reveal signs of estrogen dominance or progestogen dominance.

This procedure of adjusting the daily dose of the hormones self-administered by the female on HRT is repeated at least semi-annually or more frequently at the discretion of the attending physician during the period of HRT with the objective always being to achieve the optimal therapeutic effect with the least amount of hormones and, if desired, to maintain an amenorrhoea status. For prevention of post-menopausal osteoporosis, estradiol serum levels are not permitted to remain under 50–60 pg/ml.

EXAMPLE 2

Follow the procedure of example 1, employing a dispenser of FIGS. 2 and 3, employing tubes 55 and 56 containing the same pharmaceutical compositions as those of containers 14a and 14b, respectively, and inserts 42a and 42b of the same thickness, when a 50:50 mixture of the respective compositions are to be dispensed as the daily dose, which inserts are replaced by corresponding thicker or thiner inserts when a different ratio is to be administered, i.e., when the estrogen daily dose is to be increased or decreased and the progestogen daily dose is to remain the same, or vica versa.

EXAMPLE 3

Follow the procedure of example 1, employing a dispenser of FIGS. 4 and 5, employing a tube 60 containing in chambers 64 and 66 the same pharmaceutical compositions as those of containers 14a and 14b, respectively, and a dispensing nozzle 72a shown in FIG. 7, when a 50:50 mixture of the respective compositions are to be dispensed as the daily dose, which nozzle is replaced by corresponding nozzle 72 or 72b when a different ratio is to be administered, i.e., when the estrogen daily dose is to be increased or decreased and the progestogen daily dose is to remain the same, or vica versa.

The preceding examples can be repeated with similar success by substituting a biological equivalent of another specifically described progestogen and/or estrogen and/or dosage protocol and/or specific dispensing devices employed in the method of this invention for those used in the preceding examples.

From the foregoing description, one skilled in the art can easily ascertain that essential characteristics of this invention, and without departing from the spirit and scope thereof, can make various changes and modifications of the invention to adapt it to various usages and conditions.

What is claimed is:

1. A method for self-administration by a human female of a plurality of successive doses of an estrogen and a plurality of successive doses of a progestogen according to a protocall of self administration, wherein the female dispenses and self-administers successive individual doses of a selected volume of the estrogen and a selected volume of the progestogen over a protracted period of time, during which period of time the amount of at least one of which doses is changed, the method comprising:
   providing a first containerized source of a first extrudable pharmaceutically acceptable composition containing a plurality of non-discrete doses of the estrogen,
   providing a first meter for measuring and determining the volume of the dispensed doses of estrogen and varying the volume according to the protocall of self-administration;
   providing a second containerized source of a second extrudable pharmaceutically acceptable composition containing a plurality of non-discrete doses of the progestogen;
   providing a second meter for measuring and determining the volume of the dispensed doses of progestogen and varying the volume according to the protocall of self-administration;
   placing the first and second meters in proximity with one another wherein measured doses of estrogen and progestogen are immediately available for topical application by the patient so as to facilitate a the protocol for self-administration of the estrogen and progestogen on a repeated schedule, periodically in response to the physiological symptoms associated with menopause or the hormone replacement therapy currently exhibited by the female, so that the metered volume of at least one of the first and second compositions may be dispensed.

2. A method according to claim 1, wherein the pharmaceutical compositions are semi-solids which are dispensed as extrudates.

3. A method according to claim 1, wherein the first and second containerized sources are positioned adjacent to one another so that the pharmaceutically acceptable compositions are dispensed simultaneously from the respective sources thereof.

4. A method according to claim 1, wherein the meters have merged outputs into a mixing chamber so that dispensed doses of the first and second pharmaceutically acceptable compositions are mixed before being dispensed for application.

5. A method according to claim 1, wherein the containerized source of the first pharmaceutical composition is a first compartment of a unitary dispenser and the containerized source of the second pharmaceutical composition is a second compartment of the unitary dispenser;
   wherein the first and second pharmaceutical compositions are first extruded from their respective compartments into the first and second meters, which meters are configured as first and second metering chambers, respectively; and
   wherein the contents of the metering chambers are then formed into a single extrudate which is then dispensed through a dispenser nozzle.

6. A method according to claim 1, wherein the extrudates of the first and second pharmaceutical compositions have lengths which are extruded from the respective containerized sources which are constant and the dosage of the hormones therein is changed by changing the diameter of one or both of the extrudates, or wherein the diameter of the extrudates of the first and second pharmaceutical compositions which are extruded from the respective sources thereof is constant and the dosage of the hormones therein is changed by changing the length of one or both of the extrudates.

7. A method according to claim 1, wherein the estrogen is ethinyl estradiol or estradiol or an ester thereof, estrone, estrone sulfate or conjugated estrogens and the progestogen is micronized progesterone, norethindrone or ester thereof, norgestrel, chlornadione acetate, cyproterone acetate, desogestrel, 3-ketodesogestrel, drospirenone, norethindrone, norgestimate, levonorgestrel or gestodene.

8. A method according to claim 1, wherein the estrogen is ethinyl estradiol or 17β-estradiol and the progestogen is gestodene, levonorgestrel or 3-ketodesogestrel.

9. A method according to claim 8, wherein the pharmaceutical compositions are semi-solids;
   wherein the pharmaceutical compositions are metered from a dispenser in which the first and second containerized sources are both housed, and
   wherein the dispenser includes adjusters for changing the volumes of the pharmaceutical compositions which are dispensed from the containers in response to a defined constant digital manipulation employed to extrude the pharmaceutical compositions from the container.

10. A method for using an HRT kit for self-administration by a human female of a plurality of successive doses of an estrogen and a plurality of successive doses of a progestogen, wherein the female dispenses and self-administers successive individual doses of the estrogen and of the progestogen over a protracted period of time, during which period of time the amount of at least one of which doses is changed, which kit comprises:
    a first containerized source of a first extrudable pharmaceutically acceptable composition containing a plurality of non-discrete doses of the estrogen,
    a second containerized source of a second extrudable pharmaceutically acceptable composition containing a plurality of non-discrete doses of the progestogen,
    first and second meters in proximity with one another for receiving and indicating measured volumes of the first and second compositions thereon, wherein first and second measured doses of estrogen and progestogen are immediately available from the meters for topical application by the patient so as to facilitate a protocol for self-administration of the estrogen and progestogen on a repeated schedule, periodically in response to the physiological symptoms associated with menopause or the hormone replacement therapy currently exhibited by the female, so that a metered volume of at least one of the first and second compositions may be dispensed and applied.

11. The method of claim 10, wherein the first and second containerized sources are squeezable tubes containing the plurality of doses of estrogen and progestogen, respectively, and
    wherein the first and second meters are first and second arrays of linear markings on panel means, the first array receiving an estrogen extrudate in juxtaposition therewith and the second array for receiving a progestogen extrudate in juxtaposition therewith, whereby the ratio of estrogen to progestogen is visually apparent by the length of the extrudates on the panel means.

12. The method of claim 11 wherein the panel means is a single panel with the arrays of markings located adjacent one another thereon.

13. The method of claim 12, wherein the estrogen is ethinyl estradiol or estradiol or an ester thereof, estrone, estrone sulfate or conjugated estrogens and the progestogen is micronized progesterone, norethindrone or ester thereof, norgestrel, chlormadione acetate, cyproterone acetate, desogestrel, 3-ketodesogestrel, drospirenone, norethindrone, norgestimate, levonorgestrel or gestodene.

14. The method of claim 12, wherein the estrogen is ethinyl estradiol or 17β-estradiol and the progestogen is gestodene, levonorgestrel or 3-ketodesogestrel.

15. The method of claim 10, wherein the estrogen is ethinyl estradiol or estradiol or an ester thereof, estrone, estrone sulfate or conjugated estrogens and the progestogen is micronized progesterone, norethindrone or ester thereof, norgestrel, chlormadione acetate, cyproterone acetate, desogestrel, 3-ketodesogestrel, drospirenone, norethindrone, norgestimate, levonorgestrel or gestodene.

16. The method of claim 10, wherein the estrogen is ethinyl estradiol or 17β-estradiol and the progestogen is gestodene, levonorgestrel or 3-ketodesogestrel.

* * * * *

UNITED STATES PATENT AND TRADEMARK OFFICE
CERTIFICATE OF CORRECTION

PATENT NO. : 6,551,611 B2
DATED : April 22, 2003
INVENTOR(S) : Jörg Elliesen et al.

It is certified that error appears in the above-identified patent and that said Letters Patent is hereby corrected as shown below:

<u>Column 24,</u>
Line 13, reads "chlorondione," should read -- chlormadione --

Signed and Sealed this

Twenty-fifth Day of May, 2004

JON W. DUDAS
*Acting Director of the United States Patent and Trademark Office*